(12) United States Patent
Farazi et al.

(10) Patent No.: US 7,236,829 B1
(45) Date of Patent: Jun. 26, 2007

(54) IMPLANTABLE LEADLESS CARDIAC DEVICE WITH FLEXIBLE FLAPS FOR SENSING

(75) Inventors: Taraneh Ghaffari Farazi, San Jose, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 381 days.

(21) Appl. No.: 10/931,784

(22) Filed: Aug. 30, 2004

(51) Int. Cl.
*A61N 1/372* (2006.01)

(52) U.S. Cl. ............................. 607/36; 607/37; 607/2

(58) Field of Classification Search ............ 607/5, 607/129, 36, 119, 373, 1, 2, 4, 9; 600/508, 600/509, 510
See application file for complete search history.

(56) References Cited

U.S. PATENT DOCUMENTS

| | | | | | |
|---|---|---|---|---|---|
| 3,572,345 | A | * | 3/1971 | Auphan ..................... | 607/129 |
| 3,683,933 | A | * | 8/1972 | Mansfield .................. | 607/36 |
| 4,013,081 | A | * | 3/1977 | Kolenik ..................... | 607/9 |
| 4,256,115 | A | * | 3/1981 | Bilitch ....................... | 607/9 |
| 4,369,791 | A | * | 1/1983 | Friedman ................... | 607/36 |
| 5,230,337 | A | * | 7/1993 | Dahl et al. ................. | 607/5 |
| 5,243,977 | A | * | 9/1993 | Trabucco et al. ........... | 607/10 |
| 5,331,966 | A | * | 7/1994 | Bennett et al. ............. | 600/508 |
| 5,470,345 | A | * | 11/1995 | Hassler et al. ............. | 607/36 |
| 6,223,088 | B1 | * | 4/2001 | Scharnberg et al. ........ | 607/142 |
| 2002/0035377 | A1 | | 3/2002 | Bardy et al. ............... | 607/4 |
| 2002/0035379 | A1 | | 3/2002 | Bardy et al. ............... | 607/4 |
| 2002/0035381 | A1 | | 3/2002 | Bardy et al. ............... | 607/4 |
| 2002/0052636 | A1 | | 5/2002 | Bardy et al. ............... | 607/129 |
| 2002/0103510 | A1 | | 8/2002 | Bardy et al. ............... | 607/5 |
| 2003/0036778 | A1 | | 2/2003 | Ostroff et al. .............. | 607/9 |

FOREIGN PATENT DOCUMENTS

| | | |
|---|---|---|
| WO | WO 03/018119 A1 | 3/2003 |
| WO | WO 03/018122 A1 | 3/2003 |
| WO | WO 03/018123 A1 | 3/2003 |
| WO | WO 03/039668 A1 | 5/2003 |
| WO | WO 03/089059 A2 | 10/2003 |
| WO | WO 03/089059 A3 | 10/2003 |

\* cited by examiner

*Primary Examiner*—Carl Layno
*Assistant Examiner*—Erik J Bustamante

(57) ABSTRACT

A technique for performing sensing operations in the body subcutaneously employs, in combination, the housing of an electrical stimulator such as a pacemaker or an implantable cardioverter defibrillator and an integral flap member of flexible insulative sheet material which has at least one arm projecting away therefrom to an extreme tip end. Each arm is rolled about itself from the tip end on a lateral axis transverse of the longitudinal axis of the arm into a compact unit adjacent the housing. An incision is made through the skin and a region beneath the skin enlarged to form a cavity. The compact unit is then inserted into the cavity and unrolled about the lateral axis of each arm so as to be laid flat under the skin. When positioned into a desired orientation, each flap member is sutured to the skin to maintain the desired orientation.

12 Claims, 6 Drawing Sheets

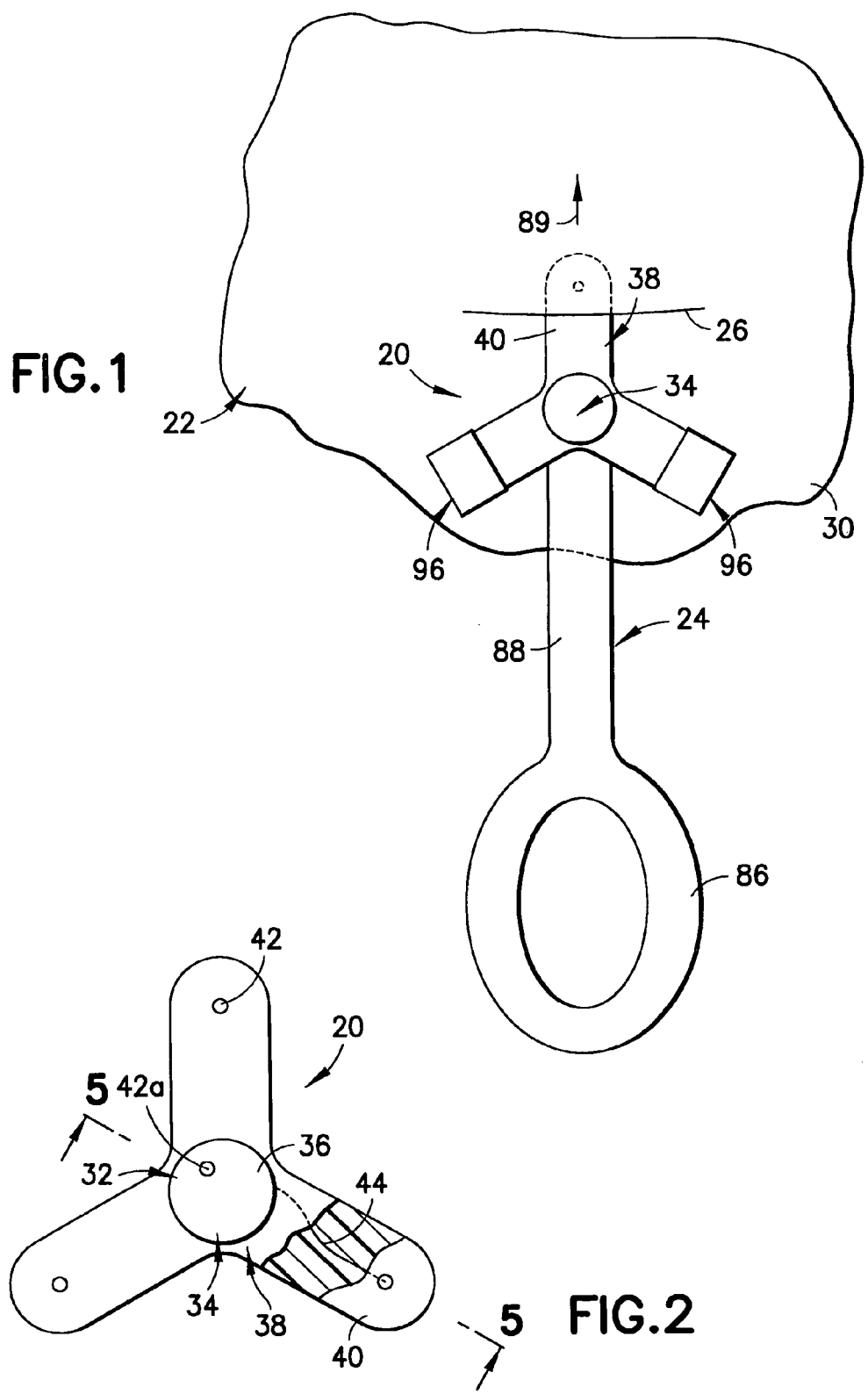

IMPLANTABLE LEADLESS CARDIAC DEVICE WITH FLEXIBLE FLAPS FOR SENSING

FIELD OF THE INVENTION

The present invention relates to implantable leadless cardiac sensing device which does not require transvenous placement.

BACKGROUND OF THE INVENTION

The requirement for pacemakers and ICDs to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, uses of transvenous lead systems, despite their many advantages, are not without their chronic patient management limitations in those with life expectancies of more than five years. The problem of lead complications is even greater in children where body growth can substantially alter transvenous lead function and lead to additional cardiovascular problems and revisions. Moreover, transvenous systems also increase cost and require specialized interventional rooms and equipment as well as special skill for insertion. These systems are typically implanted by cardiac electrophysiologists who have had a great deal of extra training.

Further, for mere sensing, the ability to implant a sensing device through a non-transverse/endocardial/epicardial, that is, subcutaneous, placement operation would be highly beneficial. By so doing, infections would be minimized and fluoroscopic imaging would not be required for the procedure.

Typical of the known prior art are a number of U.S. patent application Publications, specifically, Pub. Nos. US 2002/0035377, US 2002/0035379, US 2002/0035381, US 2002/0052636, and US 2002/0103510, all to Bardy et al. All of these disclosures relate to an apparatus and method for performing electrical cardioversion/defibrillation and optional pacing of the heart via a totally subcutaneous non-transvenous system.

Somewhat similarly, Pub. No. US 2003/0036778 to Ostroff et al. discloses a subcutaneous cardiac device which includes a subcutaneous electrode and a housing coupled to the subcutaneous electrode by a lead with a lead wire. The subcutaneous electrode is adapted to be implanted in a frontal region of the patient so as to overlap a portion of the patient's heart.

It was in light of the foregoing that the present invention was conceived and has now been reduced to practice.

SUMMARY

According to one illustrative embodiment, a technique for performing sensing operations in the body subcutaneously employs, in combination, the housing of an electrical stimulator such as a pacemaker or an implantable cardioverter defibrillator and an integral flap member of flexible insulative sheet material which has at least one arm projecting away therefrom to an extreme tip end. Each arm is rolled about itself from the tip end on a lateral axis transverse of the longitudinal axis of the arm into a compact unit adjacent the housing. An incision is made through the skin and a region beneath the skin enlarged to form a cavity. The compact unit is then inserted into the cavity and unrolled about the lateral axis of each arm so as to be laid flat under the skin. When positioned into a desired orientation, each flap member is sutured to the skin to maintain the desired orientation.

The implantable cardiac device may include one, two, or more flexible flap extensions. The device is inserted through a single incision. Each flap contains one or more sensors incorporated into it. In certain embodiments, the sensor may simply be an electrode, or may alternately be a mechanical sensor such as an accelerometer. Upon implantation, the flaps are rolled out and laid flat under the skin.

Other and further features, advantages, and benefits will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention and illustrate certain embodiments. Like numerals refer to like parts throughout the disclosure.

BRIEF DESCRIPTION OF THE DRAWINGS

The foregoing aspects and other features are explained in the following description, taken in connection with the accompanying drawings, wherein:

FIG. 1 is a top plan view illustrating the process of subcutaneously implanting a leadless cardiac device;

FIG. 2 is a top plan view of the leadless cardiac device, certain parts being cut away and shown in section;

DETAILED DESCRIPTION OF THE PREFERRED EMBODIMENTS

Figure 3:
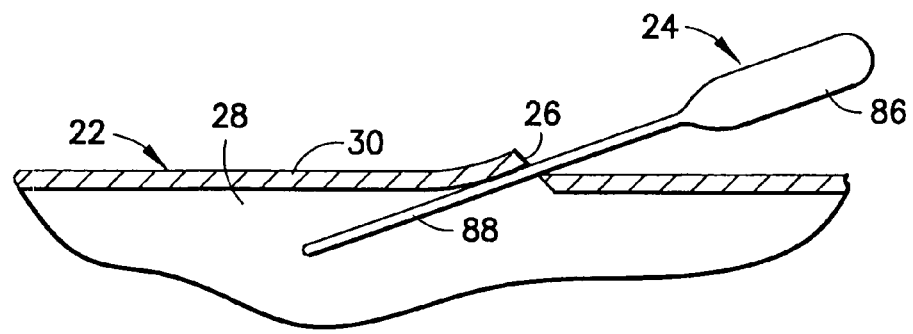
FIG. 3 is a cross section view taken through the skin of a body to receive the leadless cardiac device and illustrating one step of the implanting procedure.

Referring now to FIGS. 1 and 2, there is illustrated in top plan views, respectively, sensing apparatus 20 intended for subcutaneous implantation into a body 22. In FIG. 1, the sensing apparatus 20 has been reconfigured in a manner to be explained from its FIG. 2 form, and with the aid of a tool 24, is being inserted through an incision 26 into a cavity 28 (FIG. 3) beneath skin 30 of the body 22.

Although the present invention will be described with reference to the embodiments shown in the drawings, it should be understood that the present invention can be embodied in many alternate forms or embodiments. In addition, any suitable size, shape or type of elements or materials could be used.

The sensing apparatus 20 includes an electrical stimulator device 32 such as a pacemaker or an implantable cardioverter defibrillator (ICD) which is encased in a housing 34 having an outer peripheral surface 36. A flap member 38 of flexible insulative sheet material is mounted on the housing and includes at least one arm 40 projecting away from the housing 34. Indeed, the flap member 38 may include a plurality of arms projecting away from the housing at a plurality of peripherally spaced locations and, possibly even at a plurality of equally spaced peripheral locations. The flap member 38 is preferably composed of a nonconductive mesh fabric composed of Dacron, nylon or other suitable fiber with at least the portion of the arm or arms 40 being embedded with flexible polymeric material, silicone or polyurethane being suitable materials for the invention.

Figure 4:
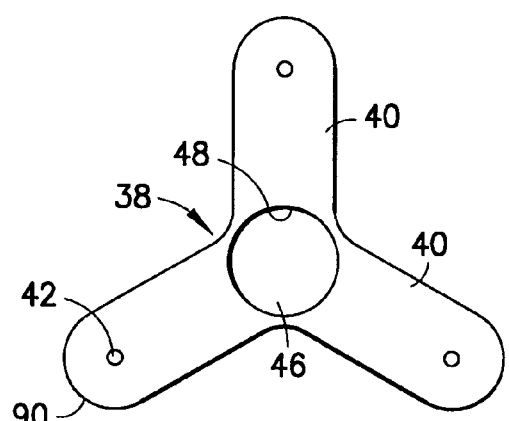
FIG. 4 is a top plan view of one component of the leadless cardiac device.
Figure 5:
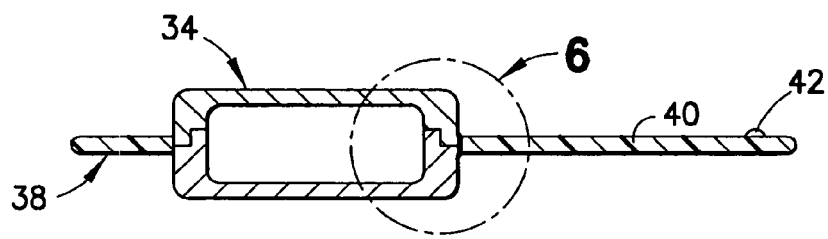
FIG. 5 is a cross section view taken generally along line 5—5 in FIG. 2.
Figure 6:
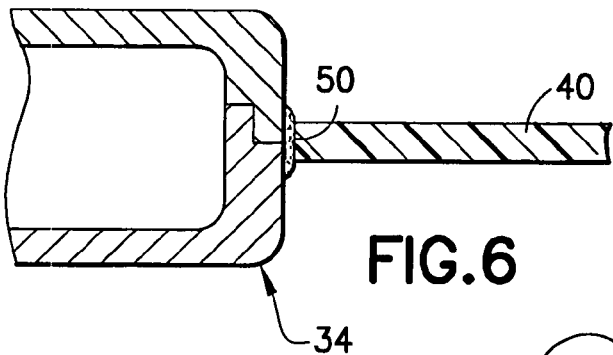
FIG. 6 is a detail cross section view of a portion of FIG. 5.

Viewing FIG. 4, the flap member 38 is seen to have an opening 46 defined by a border 48 with a continuous edge for reception of the housing 34, the continuous edge being contiguous with the outer peripheral surface 36 of the housing. As seen especially well in FIGS. 5 and 6, in this instance, suitable adhesive material 50 may be employed for firmly bonding the flap member 38 along the continuous edge of the border 48 to the housing 34.

A sensing device 42 is shown mounted on each arm 40 distant from the housing 34 and a conductor 44 electrically connects the stimulator device 32 and the sensing device. A sensing device 42a is also illustrated mounted on the housing 34 (FIG. 2) and a sensing device may also be provided inside the housing. In each instance, the sensing device may be an electrode or it may be a mechanical sensor such as an accelerometer.

Figure 7:
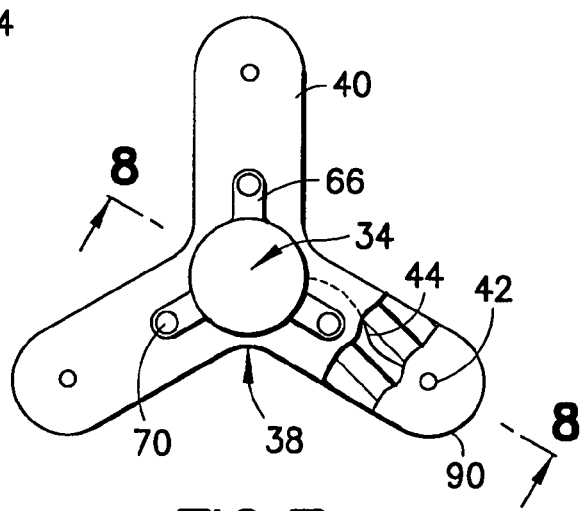
FIG. 7 is a top plan view, similar to FIG. 2, of another embodiment of the leadless cardiac device, certain parts again being cut away and shown in section.
Figure 8:
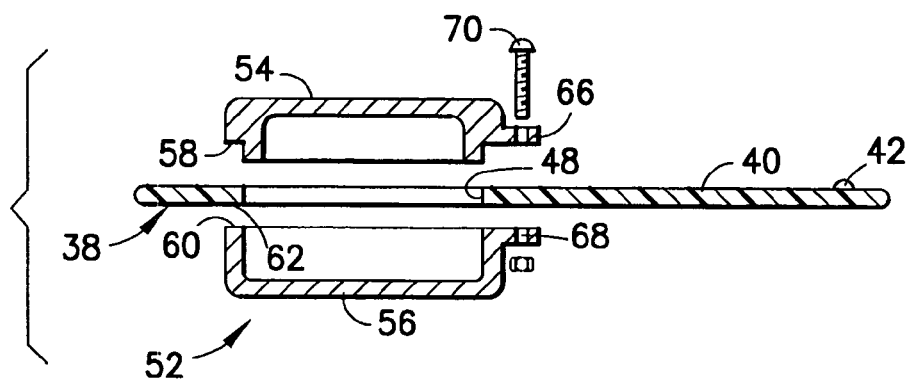
FIG. 8 is an exploded cross section view taken generally along line 8—8 in FIG. 7.
Figure 9:
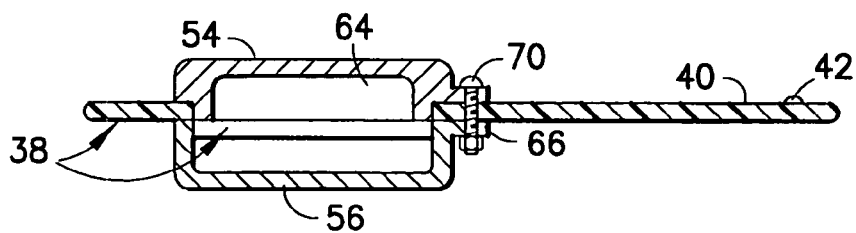
FIG. 9 is a cross section view, as FIG. 8, but with the components being integrated.

Turn now to FIGS. 7, 8, and 9 for the description of another embodiment of the invention. In this instance, the flap member 38 is generally unchanged from that illustrated in FIG. 4 and earlier described. A modified housing 52 has upper and lower shell members, 54, 56, respectively, with matingly engageable upper and lower rims 58, 60. The dimensioning is such that upon assembly of the upper and lower shell members 54, 56, the upper and lower rims 58, 60 engage and hold firm a margin 62 of the flap member 38 between the upper and lower members and, as seen in FIG. 9, fully seal the interior 64 of the housing 52 from the exterior environment. With continuing attention to FIGS. 7, 8, and 9, a plurality of lip members 66 are seen to project outwardly from the housing 52 at spaced peripheral locations. Each lip member 66 has a through bore 68 and suitable fasteners 70 are receivable through the bore of each lip member for joining together the upper and lower shell members 54, 56 of the housing 52.

Figure 10:
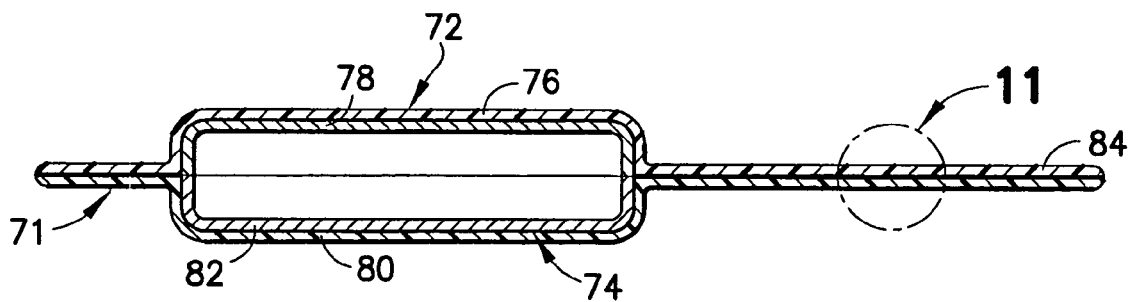
FIG. 10 is a cross section view similar to FIG. 9 of another embodiment of a leadless cardiac device.
Figure 11:
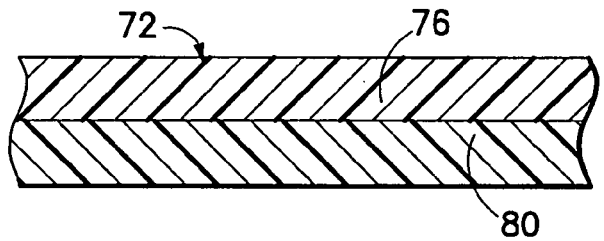
FIG. 11 is a detail cross section view of a portion of FIG. 11.

In still another embodiment of the invention, viewing FIGS. 10 and 11, a flap member 71 is composed of a mesh fabric 72 (FIG. 11) fully encapsulating a housing 74 (FIG. 10), one course 76 covering an upper shell member 78, another course 80 covering a lower shell member 82. For at least one arm 84, the flap member is embedded with flexible polymeric material such as silicone or polyurethane. As in the case of the earlier embodiments, the flap member 71 may have a plurality of arms 84 projecting away from the housing at a plurality of peripherally spaced locations.

Regardless of the particular design of the sensing apparatus, several having just been described, the subcutaneous implantation process would be uniformly performed and will now be described. To initiate the procedure, the surgeon makes the incision 26 into the skin 30 of the body 22 as seen in FIGS. 1 and 3. Thereupon, using the tool 24 including a handle 86 and longitudinally projecting blade 88, with the blade introduced through the incision 26 (in the direction of an arrow 89 in FIG. 1), the region beneath the skin 30 is enlarged to form the cavity 28 (FIG. 3) for receiving the sensing apparatus.

Figure 12:
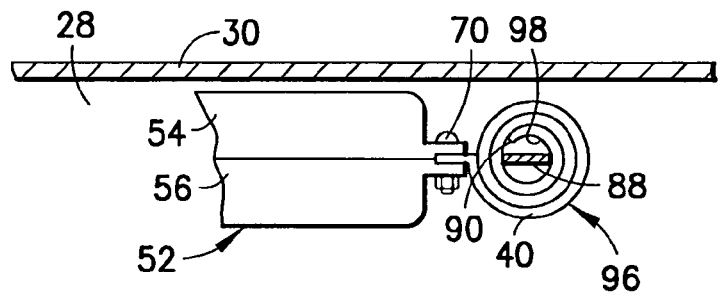
FIG. 12 is a cross section view taken through the skin of a body to receive the leadless cardiac device and illustrating the device as implanted but awaiting a further step of the implanting procedure.
Figure 13:
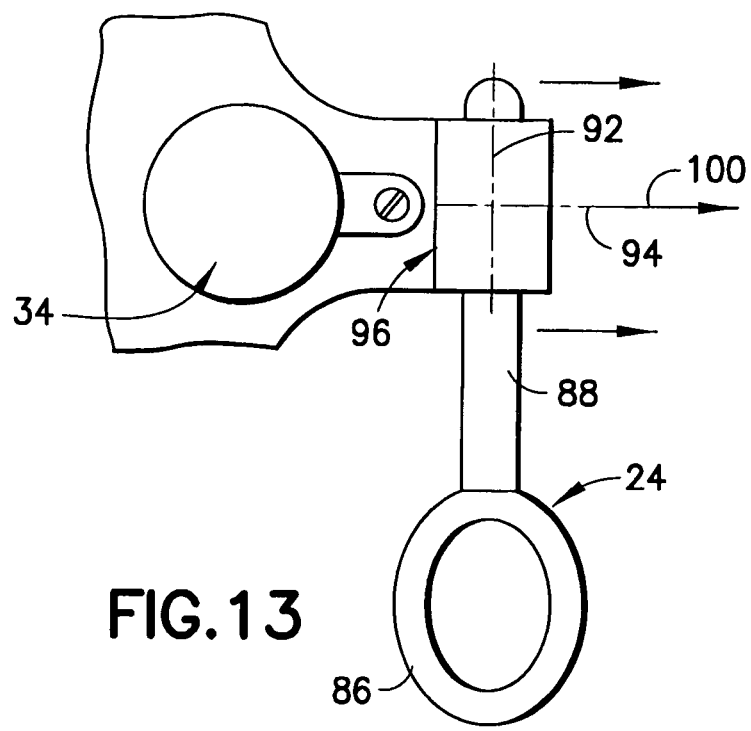
FIG. 13 is a top plan view of the components illustrated in FIG. 12.

For ease of explanation, the embodiment described with the aid of FIGS. 4 and 7 will here be referred to although the subcutaneous implantation process could be performed with any of the embodiments already described. Turn now to FIGS. 12 and 13 for a description of the process. First, an arm 40 is rolled from its tip end 90 about itself on a lateral axis 92 transverse of a longitudinal axis 94 of the arm into a compact unit 96 adjacent the housing 34, the compact unit defining an internal passage 98 aligned with the lateral axis. With the aid of the blade 88 of the tool 24, as seen in FIG. 1, the sensing apparatus 20 is inserted through the incision 26 into the cavity 28. As seen in FIG. 1, the leading arm 40 remains extended while each of the trailing arms has been rolled into the compact unit 96. Then, when the sensing apparatus 20 has been fully received into the cavity 28, each compact unit 96 is rolled out about the lateral axis 92 of its associated arm so the arm is laid generally flat under the skin to conform to the profile of the skin. To this end, the blade 88 is inserted along the lateral axis 92 through the internal passage 98 of each compact unit 96, then drawn in the direction of an arrow 100 along the axis 94 and toward the extreme tip end 90 of the arm. This procedure is repeated for each of the compact units 96 which is in place.

Figure 14:
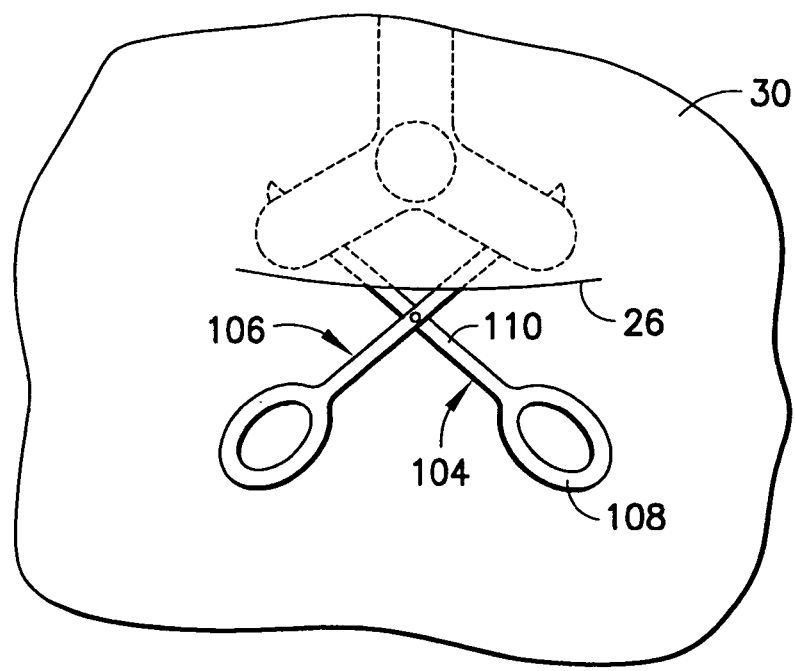
FIG. 14 is a top plan view illustrating a variation of the process of subcutaneously implanting a leadless cardiac device illustrated in FIG. 2.
Figure 15:
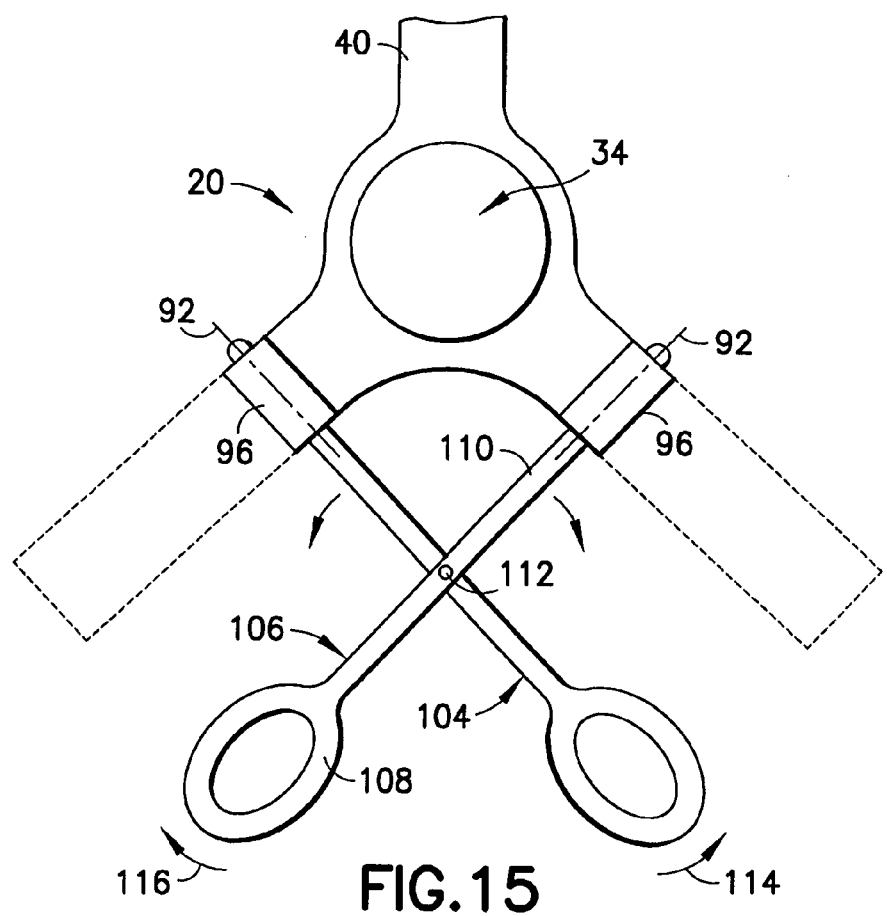
FIG. 15 is a top plan view more clearly illustrating the components illustrated in FIG. 14 and the manner of completing the process for subcutaneously implanting a leadless cardiac device.

In another instance, it may be desirable to flatten out a pair of compact units 96 simultaneously. To this end, turn now to FIGS. 14 and 15. For this procedure, a modified tool 102 is employed. The tool 102 includes first and second pivotally connected operating members 104, 106, respectively, each operating member including a handle 108 and an aligned elongated blade 110 projecting from the handle. The blades 110 have an intermediate pivotal connection 112 permitting operation of the tool 102 in the manner of a scissors. With this arrangement, the blade 110 of each operating member 104, 106 is inserted along the lateral axis 92 through the internal passage of each of a pair of the compact units 96. The handles 108 of the operating members 104, 106 are swung in the respective directions of arrows 114, 116 and, by so doing, draw the blades, respectively, toward the extreme tip end of the associated arm of the compact units. When this occurs, the compact units achieve the flattened positioning indicated in FIG. 15 by the dashed lines.

Figure 16:
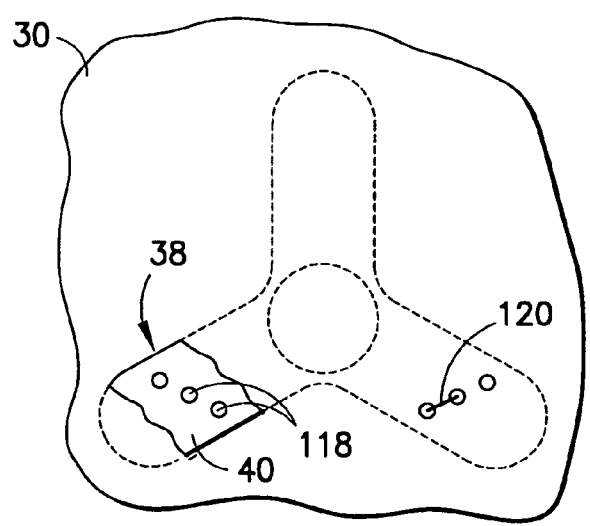
FIG. 16 is a top plan view illustrating a final step of the subcutaneous implant process, with the skin being partially cut away to illustrate the underlying leadless cardiac device.

Thereupon, the sensing apparatus is moved to a desired orientation and each of the flap members is sutured to the skin 30 to assure that the electrical stimulator device will maintain the desired orientation. This operation is seen in FIG. 16. For this purpose, each arm 40 of the flap member 38 is pierced with multiple suture holes enabling sutures 120 to appropriately attach the flap member to the body in a known manner.

Figure 17:
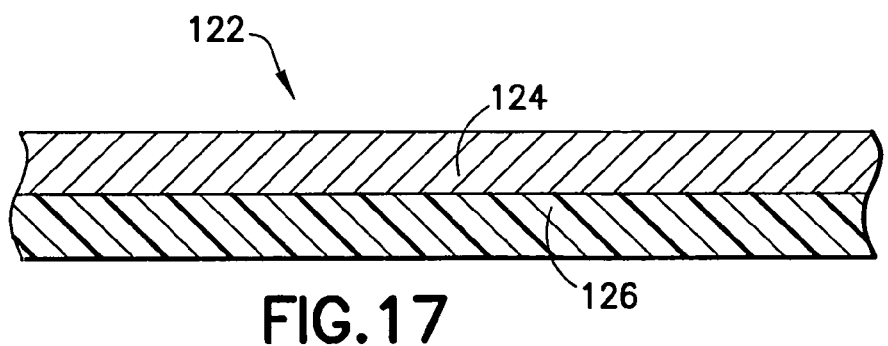
FIG. 17 is a cross section view similar to FIG. 9 of still another embodiment of a leadless cardiac device.

Yet another embodiment of the invention is illustrated in FIG. 17. In this instance, a modified flap member 122 is composed of sheet material which includes a first layer 124 of electrically conductive mesh material such as titanium mesh or platinum-iridium coil mesh or mesh of another suitable material and an opposed second layer 126 of a mesh fabric of Dacron, nylon, or other suitable fiber embedded with flexible polymeric material such as silicone, polyurethane, or other suitable material. In typical fashion, an electrode assembly utilizing the flap member 122 can be employed for sensing operations as well as for delivering electrical stimulation to the body, regardless of whether the stimulator device is a pacemaker or a defibrillator.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A subcutaneously implantable stimulation device comprising:
    an electrical stimulation and processing device comprising a housing defining an outer peripheral surface;
    a flap member of flexible insulative material connected to the housing and projecting away from the housing;
    a sensing device mounted on the flap member and spaced from the housing; and
    a conductor electrically connecting the stimulator device and the sensing device;
    wherein the flap member has an opening defined by a rim with a continuous edge;
    wherein the housing has upper and lower members with matingly engageable upper and lower rims; and
    wherein upon assembly of the upper and lower members the upper and lower rims engage and hold firm the rim of the flap member between the upper and lower members and fully seal the interior of the housing from the exterior environment.

2. A subcutaneously implantable stimulation device as set forth in claim 1:
    wherein the stimulator device is operative to perform at least one of cardioversion and defibrillation.

3. A subcutaneously implantable stimulation device as set forth in claim 1:
    wherein the stimulator device is operative to generate pacing pulses.

4. A subcutaneously implantable stimulation device as set forth in claim 1:
    wherein the flap member includes a mesh fabric at least partially embedded with flexible polymeric material.

5. A subcutaneously implantable stimulation device as set forth in claim 1:
    wherein the flap member includes a mesh fabric with an arm embedded with flexible polymeric material.

6. A subcutaneously implantable stimulation device as set forth in claim 1 including:
    wherein the flap member includes a plurality of arms projecting away from the housing at a plurality of spaced locations.

7. A subcutaneously implantable device comprising:
    a diagnostic device comprising a housing defining an outer peripheral surface;
    a flap member of flexible material mounted on the housing and projecting away from the housing;
    a sensing device mounted on the flap member and spaced from the housing; and
    a conductor electrically connecting the stimulator device and the sensing device;
    wherein the flap member has an opening defined by a rim with a continuous edge;
    wherein the housing has upper and lower members with matingly engageable upper and lower rims; and
    wherein upon assembly of the upper and lower members the upper and lower rims engage and hold firm the rim of the flap member between the upper and lower members and fully seal the interior of the housing from the exterior environment.

8. A subcutaneously implantable device as set forth in claim 7:
    wherein the diagnostic device is further operative to perform at least one of cardioversion and defibrillation.

9. A subcutaneously implantable device as set forth in claim 7:
    wherein the diagnostic device is further operative to generate pacing pulses.

10. A subcutaneously implantable device as set forth in claim 7
    wherein the flap member includes a mesh fabric at least partially embedded with flexible polymeric material.

11. A subcutaneously implantable device as set forth in claim 7
    wherein the flap member includes a mesh fabric with an arm embedded with flexible polymeric material.

12. A subcutaneously implantable device as set forth in claim 7 wherein:
    the flap member comprises a plurality of arms projecting away from the housing at a plurality of spaced locations.

* * * * *